United States Patent [19]

Ito

[11] Patent Number: 5,510,546
[45] Date of Patent: Apr. 23, 1996

[54] PROCESS FOR REARRANGING ALLYLIC GEMINAL DIHALOGEN COMPOUNDS

[75] Inventor: Larry N. Ito, Midland, Mich.

[73] Assignee: The Dow Chemical Company, Midland, Mich.

[21] Appl. No.: 499,692

[22] Filed: Jul. 7, 1995

[51] Int. Cl.⁶ .................................................. C07C 21/04
[52] U.S. Cl. ............................................................ 570/236
[58] Field of Search ............................................. 570/236

[56] References Cited

U.S. PATENT DOCUMENTS 5,072,063  12/1991  Langensee ........................... 570/236

*Primary Examiner*—Alan Siegel

[57] ABSTRACT

An improved process for converting 3,3-dichloropropene in an intermediate boiling byproduct stream from a process of making allyl chloride by the chlorination of propylene to cis- or trans-1,3-dichloropropene or a mixture of these, wherein the intermediate boiling byproduct stream is processed batchwise or continuously to dry the stream to a water content of less than about 15 parts per million by weight, and then is contacted in the liquid phase with an alumina, silica or zeolite catalyst under conditions effective to carry out the conversion.

14 Claims, No Drawings

PROCESS FOR REARRANGING ALLYLIC GEMINAL DIHALOGEN COMPOUNDS

BACKGROUND OF THE INVENTION

A significant by-product in the important commercial process of producing allyl chloride through the chlorination of propylene is 3,3-dichloropropene. Unfortunately, 3,3-dichloropropene and its homologs do not have a significant commercial use, so that the 3,3-dichloropropene produced in this manner has heretofore usually been incinerated.

As related in U.S. Pat. No. 5,072,063 to Langensee (hereafter, "Langensee"), a number of efforts have been made at the same time to produce the 1,3-dichloropropenes also produced as byproducts in the allyl chloride process, because of the known utility of both the cis- and trans-isomers of 1,3-dichloropropene as, for example, nematocides (German Patent Application No. 1,210,618), soil fumigants, insecticides and monomers in the production of plastics, resins and chemical intermediates.

These past efforts have included reacting 1,2-dichloropropane with a gas containing oxygen in the presence of a catalyst containing $CuCl_2$, $LiCl$ and $ZnCl_2$ at 470 to 490 deg. Celsius, dehydrochlorination of 1,2,3-trichloropropane in the presence of oxygen or halogen, contacting 1,2-dichloropropane with chlorine to effect both chlorination and dechlorination reactions, or mixing 1,2-dichloropropane with allyl chloride and/or 1-chloropropene and reacting with chlorine at high temperature.

Langensee elected, in view of the availability and lack of utility of 3,3-dichloropropene and further citing the complicated, energy-consuming and/or inconvenient nature of the aforementioned processes, to pursue the isomerization of a 3,3-dihalopropene generally and 3,3-dichloropropene more particularly to the respective 1,3-dihalopropenes or 1,3-dichloropropenes and homologs thereof. This isomerization was accomplished by contacting the 3,3-dichloropropene with an alumina, silica or zeolite catalyst, and especially an alumina, silica or zeolite having acidic sites, in preferably a fixed bed, continuous process. In particular, Langensee contemplated the isomerization would be conducted directly on a 3,3-dichloropropene-containing, intermediate boiling byproduct stream from a distillation of the product stream from an allyl chloride process, to produce cis- and trans-1,3-dichloropropenes to be combined with the cis- and trans-1,3-dichloropropenes otherwise produced in the allyl chloride process and recovered through distillation.

An earlier Japanese patent, JP 80-69,523, was cited for also teaching an isomerization process, involving contacting 3,3-dichloropropene in the presence of hydrogen chloride with a catalytic amount of a zinc, iron, copper, tin, titanium or vanadium salt at between 0 degrees and 200 degrees Celsius. The difficulty found by Langensee with respect to the Japanese process, however, was that the catalyst was suspended in the reaction mixture and difficult to remove from the reaction mixture after completion of the rearrangement process.

SUMMARY OF THE PRESENT INVENTION

The present invention provides a significant further improvement on the isomerization processes taught in Langensee and the earlier Japanese patent, and comprises a process for preparing cis- or trans-1,3-dichloropropene (or homologs thereof) or a mixture of these, or for preparing the 1,3-dibromopropenes, wherein a 3,3-dichloro- or 3,3-dibromopropene-containing feed which also includes water therein is dried to remove at least some of the water from the feed, and then contacted with an alumina, silica or zeolite catalyst according to Langensee's teachings under conditions effective to carry out the desired rearrangement.

The 3,3-dichloropropene in an intermediate boiling byproduct stream from a distillation of the products of a conventional process for making allyl chloride by the chlorination of propylene is particularly of interest for processing according to the present invention. Generally this intermediate boiling byproduct stream is in a suitably dry condition already, and need not be dried in accord with the present invention where the byproduct stream is directly processed over a suitable alumina, silica or zeolite catalyst.

It has presently been discovered, however, that where the 3,3-dichloropropene (3,3-DCPe) source stream is not so directly processed, water such as may be picked up by the source stream in storage or through other means has a significantly adverse impact on at least the rate of deactivation and productivity seen in further processing the stream according to the process described in Langensee.

DETAILED DESCRIPTION OF PREFERRED EMBODIMENTS

In a broad sense, the materials which may be isomerized by the present process are those contemplated in Langensee, and are of the general Formula I as follows:

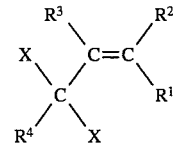

wherein X represents chloro and $R^1$, $R^2$, $R^3$, and $R^4$ independently represent hydrogen or a $C_1$–$C_3$ straight chain or branched chain alkyl group (e.g., methyl, ethyl, propyl and 1-methylethyl), or wherein X is bromo and each of $R^1$, $R^2$, $R^3$, and $R^4$ is hydrogen.

Compounds of this Formula I wherein X is chloro and $R^1$, $R^2$, $R^3$ and $R^4$ independently are hydrogen or a methyl group are preferred, as are compounds wherein each of $R^1$, $R^2$, $R^3$ and $R^4$ are hydrogen.

The products of the isomerization process of the present invention in the same broad sense are corresponding dichloroalkenes or dibromoalkenes of Formula II or Formula III:

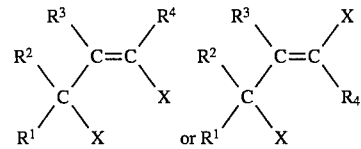

wherein X is chloro and $R^1$, $R^2$, $R^3$ and $R^4$ independently are hydrogen or a $C_1$–$C_3$ straight chain or branched chain alkyl group, or X is bromo and each of $R^1$, $R^2$, $R^3$ and $R^4$ is hydrogen. Within this class of products, compounds wherein X is chloro and $R^1$, $R^2$, $R^3$ and $R^4$ independently are hydrogen or a methyl group are preferred, as are compounds wherein each of $R^1$, $R^2$, $R^3$ and $R^4$ is hydrogen.

Isomerization of 3,3-dichloropropene (3,3-DCPe) is again especially of interest, such material being conventionally contained in an intermediate boiling point by-product fraction from the distillation of the product stream from a process of making allyl chloride by the chlorination of propylene, for example as disclosed in U.S. Pat. No. 4,319,062 to Boozalis et al., such patent being incorporated herein by reference. As has been noted previously, 1,3-dichloropropene in either the cis- or trans- configuration is correspondingly preferred as a product. Generally, some of both isomers is produced, and the present invention contemplates the production of either of these isomers or a mixture of these.

The intermediate boiling fraction that remains after removing a lower boiling fraction containing the desired allyl chloride product and higher boiling fractions containing most of the cis- and trans-1,3-dichloropropenes includes a variety of inert (to the alumina, silica and zeolite catalysts contemplated for the present process) chlorinated propanes and propenes, of which generally between about 10 and 20 percent by total weight is the targeted 3,3-dichloropropene. Other byproducts of the allyl chloride process include the just-mentioned cis- and trans-1,3-dichloropropenes, 2,3-dichloropropene, 2,2-dichloropropane, 1,2-dichloropropane and related species, with 1,2-dichloropropane being present generally as a major component at from approximately 50 percent to 85 percent by weight, and typically from about 60 to 75 percent by weight.

According to the improved process of the present invention in a most preferred embodiment, such an intermediate boiling fraction containing 3,3-DCPe and further containing generally about 100 parts per million by weight of water or greater, is dried to a water content of preferably less than about 50 parts per million by weight, but more preferably less than about 30 parts per million by weight and most preferably less than about 15 parts per million by weight.

The drying step can be performed by any known means for doing so, a preferred, exemplary means involving passing the byproduct stream over molecular sieves or other water-absorbing materials conventionally used in drying applications at essentially ambient temperatures. Thereafter, the dried byproduct stream is preferably exposed to a heterogeneous, solid alumina, silica or zeolite catalyst in the manner described in Langensee, U.S. Pat. No. 5,072,063 to Langensee accordingly being incorporated herein by reference for its teachings as to the conversion process and the catalysts useful therein.

Focusing now on the isomerization process and catalysts taught in Langensec, naturally-occurring and synthetic aluminas, silicas and zeolites are contemplated which have large specific surface areas of from about 50 to about 700 square meters per gram. Aluminas, and especially acidic, activated aluminas, are indicated to be more generally preferred but specific preferred examples are given also of acidic silica gels and the acidic forms of zeolites A, X and Y. Mixtures of one or more of these are also contemplated, in small particulate form, in the form of pellets, extrudates, spheres, tablets, granules or other shaped forms.

Generally the isomerization process can be carried out batchwise or continuously, with a fixed bed, continuous process being preferred but a fluidized bed process also being possible. Process temperatures are broadly taught in Langensee as ranging from about 0 degrees Celsius up to about 130 degrees Celsius, but preferably are from about 20 degrees Celsius to about 120 degrees Celsius, and more preferably are from about 50 degrees Celsius to about 110 degrees Celsius. Any pressure can be used, but preferably the pressure and temperature are selected so that substantially all of the components of the byproduct stream fed to the isomerization process remain in the liquid state, exemplary pressures being from ambient pressure up to about 1500 kPa. Reaction times are stated as varying with the starting material to be isomerized, the process temperature, catalyst and reactor type employed. Exemplary batch times for a batchwise process are reported as being from about 0.5 to about 8 hours, and generally falling in the range of from about 1.5 to about 4 hours. A fixed bed residence time in a continuous process of from about 1 to about 300 minutes is considered generally sufficient, with times of from about 2 to about 180 minutes, and especially from about 2 to about 120 minutes being preferred.

The improvement offered by the present invention in the context of such a process is more particularly illustrated by the following examples:

Examples 1 and 2

A 3,3-dichloropropene-containing, intermediate boiling fraction from a distillation of the products of a commercial allyl chloride process, containing about 100 parts per million by weight of water, was dried over molecular sieves at room temperature (about 20 degrees Celsius) to a water content of about 15 parts per million by weight. The dried feed was then passed at 6.0 ml per hour over an acidic activated alumina (pH of 6.54 in aqueous slurry) sold by Norton Chemical Process Products with the designation SA-6275, which had been ground and sieved to a 14 by 20 mesh (1.4 mm. by 0.85 mm). Five (5.0) cubic centimeters of the alumina catalyst were employed for this step in a 316 stainless steel, 0.5 inch O.D. liquid phase tubular reactor maintained at 130 pounds per square inch, gauge and at 90 degrees Celsius for one run, and 120 degrees for a second run with a second dried feed portion. For the run at 90 degrees, the maximum conversion seen of 3,3-DCPe to the cis- and trans- isomers of 1,3-dichloropropene was 99.1 percent, the rate of catalyst deactivation was determined to be 0,088 percent per hour, and the catalyst productivity was 25.9 grams of 3,3-DCPe isomerized per gram of catalyst. For the run at 120 degrees, the maximum conversion was 98.9 percent, the deactivation rate was 0.024 percent per hour, and the productivity was assessed at 94.9 grams of 3,3-DCPe converted per gram of catalyst.

Comparative Examples 1 and 2

The runs in Examples 1 and 2 were repeated for comparison without the initial drying step. The run at 90 degrees showed a maximum conversion of 80.5 percent, a deactivation rate of 0.83 percent conversion loss per hour, and a productivity of 1.08 grams of 3,3-DCPe isomerized per gram of catalyst. The run at 120 degrees had a maximum conversion of 98.6 percent, but a deactivation rate of 0.15 percent conversion loss per hour and a productivity of 15.2 grams of 3,3-DCPe isomerized per gram of catalyst.

The results from Examples 1 and 2 and those from Comparative Examples 1 and 2 are compiled in Table 1 below:

TABLE 1

| T (°C.) | Feed | Max. Conv. (%) | DR (%/hr) | Prod.[a] |
|---|---|---|---|---|
| 90 | W/o Drying | 80.5 | 0.83 | 1.08 |
|  | W/Drying | 99.1 | 0.088 | 25.9 |
| 120 | W/o Drying | 98.6 | 0.15 | 15.2 |
|  | W/Drying | 98.9 | 0.024 | 94.9 |

[a] Productivity in grams 3,3DCPe converted per gram catalyst

What is claimed is:

1. In a process for preparing a dihaloalkene compound of the formula

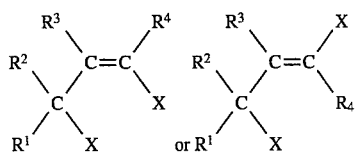

wherein

X represents chloro or bromo

R$^1$, R$^2$, R$^3$, and R$^4$ independently represent hydrogen or a C$_1$–C$_3$ alkyl group, with the proviso that when X represents bromo each of R$^1$, R$^2$, R$^3$, and R$^4$ represents hydrogen or a mixture of such compounds, which process comprises contacting a dihaloalkene compound of the formula

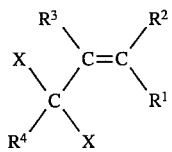

wherein

X represents chloro or bromo and

R$^1$, R$^2$, R$^3$, and R$^4$ independently represent hydrogen or a C$_1$–C$_3$ alkyl group, with the proviso that when X represents bromo each of R$^1$, R$^2$, R$^3$, and R$^4$ represents hydrogen in the liquid state with an effective catalyst selected from the group consisting of aluminas, silicas and zeolites under conditions effective to carry out the conversion, the improvement which comprises drying the dihaloalkene compound to be processed in said process or a stream or aggregation comprising the dihaloalkene compound to be so processed, prior to contacting the dihaloalkene compound with the alumina, silica or zeolite catalyst.

2. A process as defined in claim 1, wherein the dihaloalkene compound contacted with the catalyst is 3,3-dichloropropene.

3. A process as defined in claim 2, wherein the 3,3-dichloropropene starting material is a component of an intermediate boiling byproduct stream derived from the distillation of the products of a process for making allyl chloride by the chlorination of propylene.

4. A process as defined in claim 3, wherein cis- or trans-1,3-dichloropropene or a mixture of these are produced from the 3,3-dichloropropene in the intermediate boiling byproduct stream.

5. A process as defined in claim 4, wherein the drying step is conducted by contacting the intermediate boiling byproduct stream with a molecular sieve material at essentially ambient temperatures.

6. A process as defined in claim 4, wherein the intermediate boiling byproduct stream is dried to a water content of less than about 50 parts per million by weight.

7. A process as defined in claim 6, wherein the intermediate boiling byproduct stream is dried to a water content of less than about 30 parts per million by weight.

8. A process as defined in claim 7, wherein the intermediate boiling byproduct stream is dried to a water content of less than about 15 parts per million by weight.

9. A process as defined in claim 6, wherein the catalyst is an alumina.

10. A process as defined in claim 1, wherein the catalyst is an alumina.

11. A process as defined in claim 6, wherein the dried intermediate boiling byproduct stream is contacted with the catalyst at a temperature between about 90 degrees Celsius and about 130 degrees Celsius or greater, up to the degradation temperature of the 1,3-dichloropropene product.

12. A process as defined in claim 1, wherein the dihaloalkene or the stream or aggregation comprising the dihaloalkene is contacted with the catalyst at a temperature between about 90 degrees Celsius and about 130 degrees Celsius or greater, up to the degradation temperature of the dihaloalkene product.

13. A process as defined in claim 6, wherein the drying and conversion steps are carried out in a continuous manner.

14. A process as defined in claim 1, wherein the drying and conversion steps are carried out in a continuous manner.

* * * * *